US012161783B1

United States Patent
Fang (10) Patent No.: US 12,161,783 B1
(45) Date of Patent: Dec. 10, 2024

(54) ROTARY DRIPPING AROMATHERAPY HUMIDIFIER

(71) Applicant: Limei Fang, Ganzhou (CN)

(72) Inventor: Limei Fang, Ganzhou (CN)

( * ) Notice: Subject to any disclaimer, the term of this patent is extended or adjusted under 35 U.S.C. 154(b) by 0 days.

(21) Appl. No.: 18/642,903

(22) Filed: Apr. 23, 2024

(30) Foreign Application Priority Data

Mar. 19, 2024 (CN) .......................... 202420535459.0

(51) Int. Cl.
 *A61L 9/14* (2006.01)
 *F24F 6/00* (2006.01)
 *F24F 6/12* (2006.01)

(52) U.S. Cl.
 CPC .................. *A61L 9/14* (2013.01); *F24F 6/12* (2013.01); *A61L 2209/135* (2013.01); *F24F 2006/003* (2013.01); *F24F 2006/008* (2013.01)

(58) Field of Classification Search
 CPC ........ A61L 9/14; A61L 2209/135; F24F 6/12; F24F 2006/003; F24F 2006/008
 See application file for complete search history.

(56) References Cited

U.S. PATENT DOCUMENTS

| 6,978,564 B2 * | 12/2005 | Hou | ........................ | G09F 19/02 |
| | | | | 40/406 |
| 2013/0154131 A1 * | 6/2013 | Hou | ..................... | B01F 23/213 |
| | | | | 261/24 |

FOREIGN PATENT DOCUMENTS

| CN | 208832648 U | | 5/2019 |
| CN | 215982994 U | | 3/2022 |
| CN | 114608190 A | * | 6/2022 |
| CN | 216977043 U | | 7/2022 |
| CN | 220601685 U | | 3/2024 |

* cited by examiner

Primary Examiner — Sean E Conley
Assistant Examiner — Brendan A Hensel
(74) Attorney, Agent, or Firm — Nitin Kaushik (57) ABSTRACT

The present disclosure relates to a rotary dripping aromatherapy humidifier, including a water tank. An atomizing module and a power output component are fixedly provided below the water tank, a driving gear is provided on the power output component and is positioned inside the water tank, a middle frame is covered on the water tank, a penetrating opening is provided on the middle frame, a hollow water supply bracket is provided within the penetrating opening, a transmission gear is provided below the water supply bracket, water leakage holes and at least one first through hole are provided in the middle frame, and a first gear tray is provided below the middle frame. The rotary dripping aromatherapy humidifier of the present disclosure is designed with rotationally arranged decorative pieces, and can achieve a dripping effect, thus providing a better visual effect than the traditional aromatherapy machines.

10 Claims, 9 Drawing Sheets

ROTARY DRIPPING AROMATHERAPY HUMIDIFIER

CROSS-REFERENCE TO RELATED APPLICATIONS

The application claims priority to Chinese patent application No. 2024205354590, filed on Mar. 19, 2024, the entire contents of which are incorporated herein by reference.

TECHNICAL FIELD

The present disclosure belongs to the field of aromatherapy machines, and particularly relates to a rotary dripping aromatherapy humidifier.

BACKGROUND

In the field of aromatherapy humidifiers, due to limitation of the traditional design and technical restrictions, the appearances and the functions of the existing aromatherapy humidifiers are relatively simple. For example, the adoption of the traditional cylindrical or square design lacks unique appearance characteristics and is difficult to attract the attention of consumers. Moreover, in terms of the display effect, most of the aromatherapy humidifiers only have the spraying function and lack of fun. The present disclosure aims to provide an aromatherapy humidifier with a better appearance and better use experience.

SUMMARY

In view of the above, the present disclosure provides a rotary dripping aromatherapy humidifier.

To achieve the purposes, the present disclosure provides the technical solution as follows: a rotary dripping aromatherapy humidifier includes a water tank, where an atomizing module and a power output component are fixedly provided below the water tank, a driving gear is provided on the power output component, the driving gear is positioned inside the water tank, and a middle frame is covered on the water tank;

a penetrating opening is provided on the middle frame, a hollow water supply bracket is provided within the penetrating opening, and a transmission gear is provided below the water supply bracket; and water leakage holes and at least one first through hole are provided in the middle frame, a first gear tray is provided below the middle frame, a gear avoiding hole for the transmission gear to pass through is provided in the first gear tray, rotatable driven gears corresponding to the first through holes are provided between the first gear tray and the middle frame, and rotary decorative pieces are fixedly provided on the driven gears.

Further, the water supply bracket is rotatably arranged at the penetrating opening, a lower part of the water supply bracket is fixedly connected to the transmission gear, and the water supply bracket rotates together with the transmission gear during rotation of the transmission gear.

Further, the water supply bracket is fixedly arranged in the penetrating opening.

Further, a limiting component is fixedly provided below the penetrating opening, and the transmission gear is rotatably arranged on an outer side of the limiting component or below the water supply bracket.

Further, the driving gear, the transmission gear and the driven gears are in engaged transmission, and the rotary decorative pieces are driven by the driven gears to rotate during rotation of the driven gears.

Further, a second gear tray configured for supporting the transmission gear is provided below the transmission gear, a water supply hole is provided in the second gear tray, and the second gear tray is fixed below the water supply bracket or below the penetrating opening.

Further, a bearing is provided on an outer side of the water supply bracket or on an inner side of the transmission gear.

Further, a water storage tray is provided at an upper end of the water supply bracket, and drip holes for dripping water are provided in the water storage tray.

Further, a top cover is covered on the upper part of the water storage tray, a spray outlet hole is provided in the top cover, and a water baffle is provided below the spray outlet hole.

Further, the rotary decorative pieces are annularly arranged on the middle frame, and the water supply bracket is arranged at the center of the rotary decorative pieces.

Compared with the existing technology, the rotary dripping aromatherapy humidifier provided by the present disclosure has the advantages as follows:

The rotary dripping aromatherapy humidifier is designed with the rotationally arranged decorative pieces, and can achieve a dripping effect, thereby providing a better visual effect than the traditional aromatherapy machines.

The rotary dripping aromatherapy humidifier can further achieve rotation of a dripping component and the rotary decorative pieces, providing better use experience.

BRIEF DESCRIPTION OF DRAWINGS

To illustrate the technical solution in embodiments of the present disclosure more clearly, a brief introduction regarding the drawings needed to be used for describing the embodiments or the existing technology is given below, it is obvious that the drawings in the following description are only some embodiments of the present disclosure, and persons of ordinary skill in the art can obtain other drawings according to these drawings without creative effort.

| Name | Numeral | Name | Numeral | Name | Numeral |
|---|---|---|---|---|---|
| Water tank | 1 | Power output component | 11 | Atomizing module | 12 |

-continued

| Name | Numeral | Name | Numeral | Name | Numeral |
|---|---|---|---|---|---|
| Control circuit board | 13 | Water-guiding pipe | 14 | | |
| Bottom housing | 16 | Top cover | 17 | Spray outlet hole | 171 |
| Middle frame | 2 | Water leakage hole | 21 | Penetrating opening | 22 |
| First through hole | 23 | | | | |
| Driving gear | 4 | Transmission gear | 41 | Driven gear | 42 |
| First gear tray | 5 | Gear avoiding hole | 51 | Second gear tray | 6 |
| Water supply hole | 61 | | | | |
| Water supply bracket | 7 | Drip hole | 71 | Water baffle | 72 |
| Water storage tray | 73 | Position-limiting component | 9 | | |
| Rotary decorative piece | 8 | | | | |

DETAILED DESCRIPTION OF THE EMBODIMENTS

To better understand the technical solution of the present disclosure, the embodiments provided by the present disclosure will be described in detail with reference to the drawings.

The rotary dripping aromatherapy humidifier provided by the embodiments of the present disclosure is described in detail above, according to the ideas of the embodiments of the present disclosure. For persons of ordinary skill in the art, in light of the ideas of the embodiments of the present disclosure, there will be changes in the specific implementation mode and the application scope. In summary, the contents of the specification should not be understood as the limitation to the present disclosure.

In the description of the present disclosure, it should be understood that orientation or position relationships indicated by the terms such as "length", "width", "upper", "lower", "middle", "front", "back", "left", "right", "vertical", "horizontal", "top", "bottom", "inside" and "outside" are the orientation or position relationships shown based on the drawings. These terms are used only for facilitating the description of the present disclosure and for simplifying the description, rather than indicating or implying that the referred apparatuses or elements must have specific orientations and must be constructed and operated in the specific orientations, and therefore cannot be understood as the limitation to the present disclosure.

In the present disclosure, unless otherwise expressly specified and defined, the terms such as "arranged", "connected to", "connection" and "fixed" should be broadly understood, for example, can be a fixed connection, a detachable connection or an integration, can be either a mechanical connection or an electrical connection, can be either a direct connection, or an indirect connection through a medium, can be either an internal connection of two elements, or an interaction between two elements. Persons of ordinary skill in the art can understand the specific meanings of the above terms in the present disclosure according to specific circumstances.

As shown in FIGS. 1 to 9, the embodiments of the present disclosure provide a rotary dripping aromatherapy humidifier.

Figure 1:
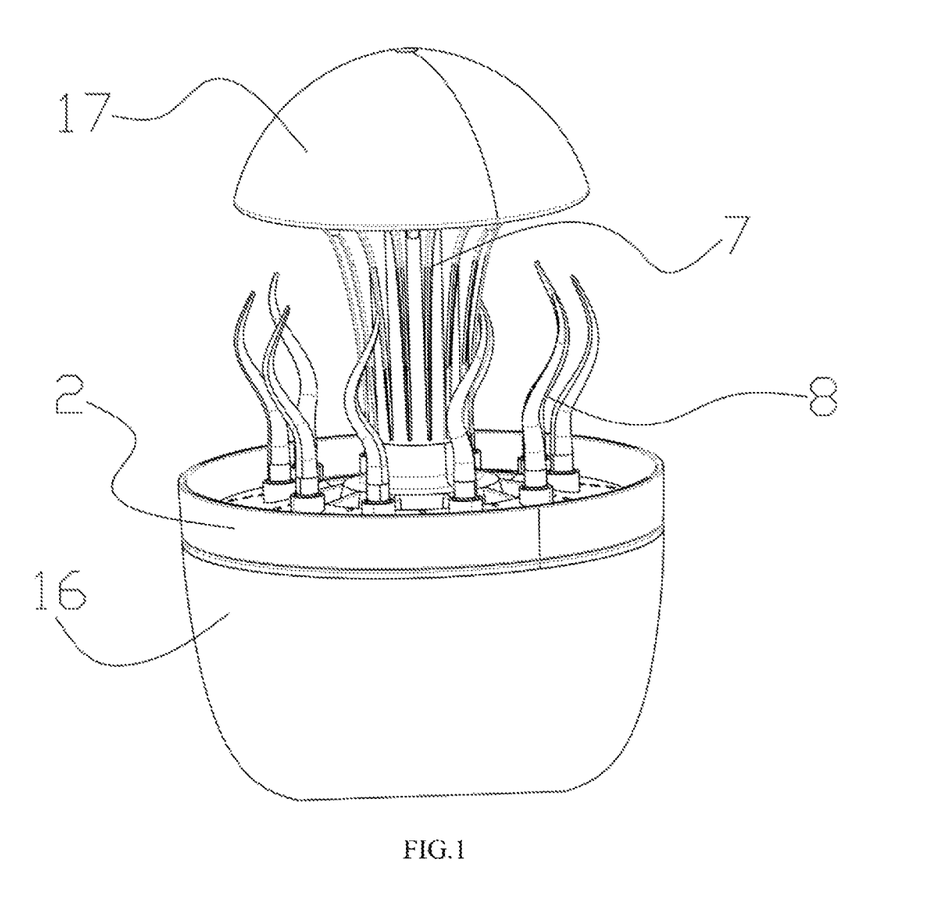
FIG. 1 is an overall structural diagram of Embodiment 1 of the present disclosure.
Figure 2:
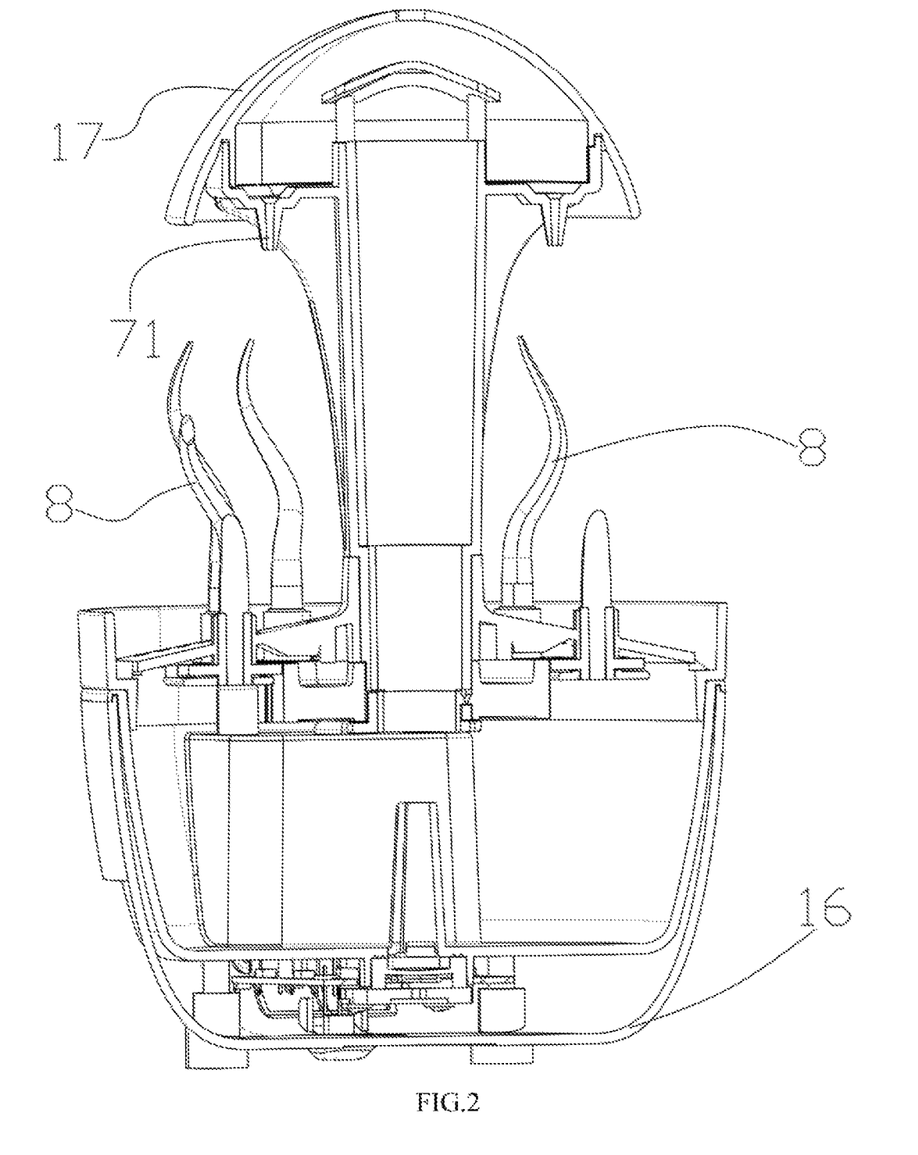
FIG. 2 is a schematic sectional view of Embodiment 1 of the present disclosure.
Figure 6:
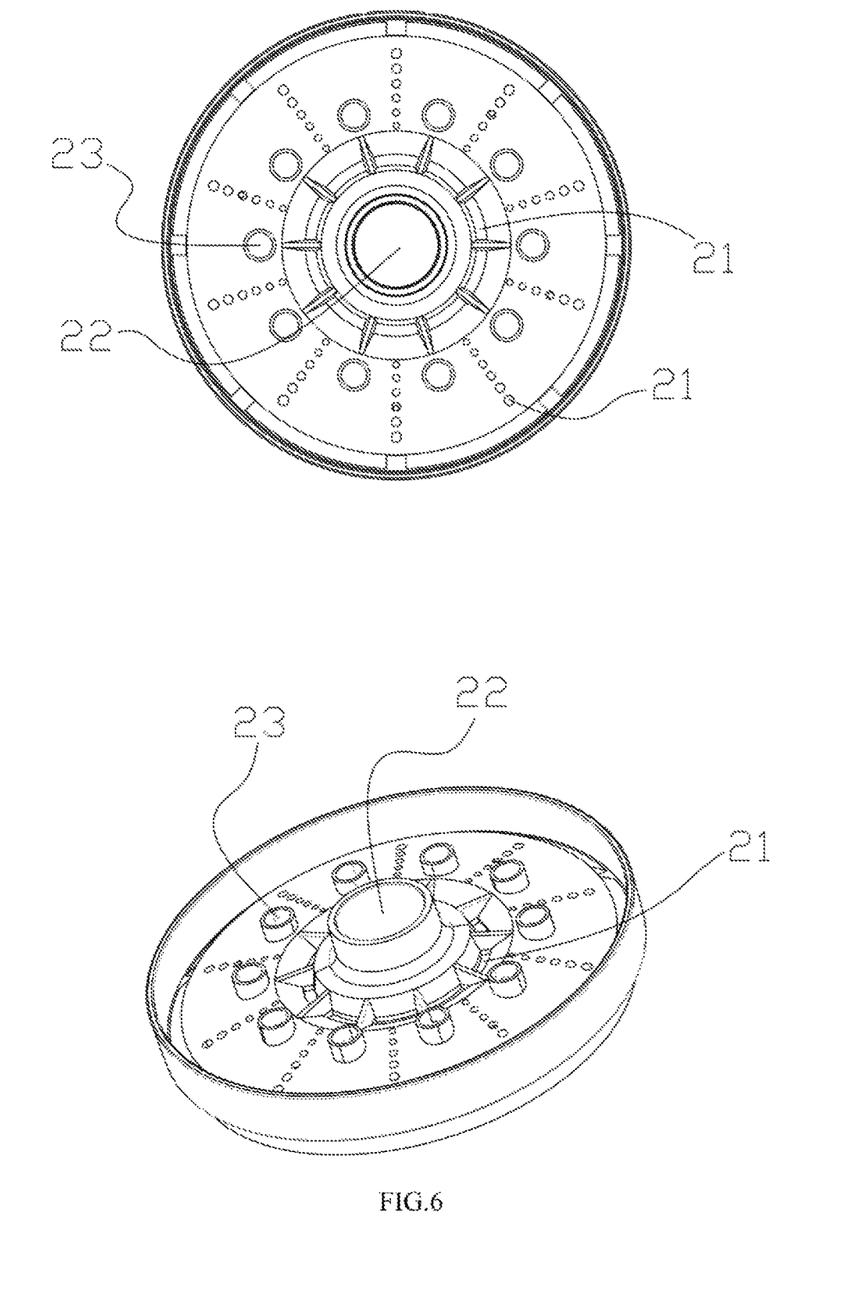
FIG. 6 is a schematic structural diagram of the middle frame of Embodiment 1 of the present disclosure.

As shown in FIGS. 1 to 2 and FIG. 6, the rotary dripping aromatherapy humidifier includes a water tank 1, a bottom housing 16, a bracket and a middle frame 2. After the water tank 1 is fixed on the bottom housing 16, related components such as a control circuit board 13, buttons and a power output component 11 are fixed in an enclosed area defined by the bottom housing 16 and the water tank 1. Related electronic components are electrically connected to the control circuit board and are controlled by the buttons. A bin for accommodating the power output component 11 is provided at the bottom of the water tank 1, and the power output component 11 is fixedly arranged within the bin. An atomizing hole is provided in the bottom of the water tank 1, and an atomizing module 12 for atomizing water in the water tank 1 is fixedly provided below the atomizing hole.

Figure 5:
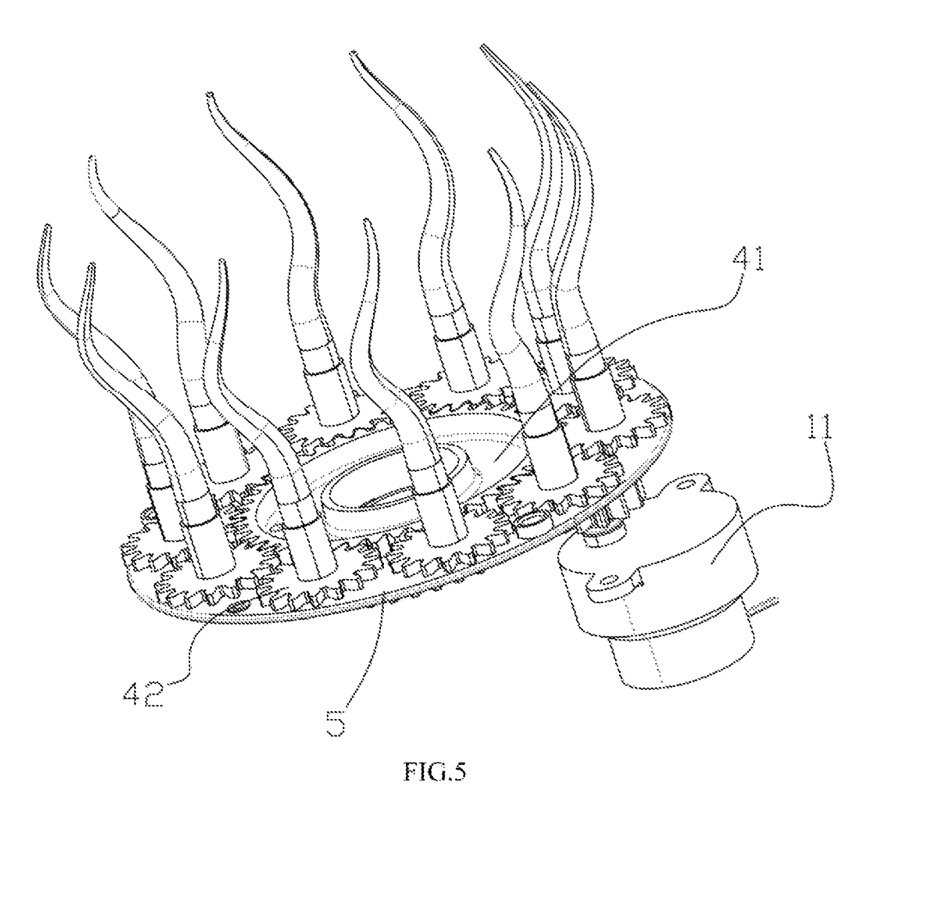
FIG. 5 is a schematic structural diagram of the first gear tray of Embodiment 1 of the present disclosure.

As shown in FIG. 5, the opening of the water tank 1 is covered by the middle frame 2. A plurality of water leakage holes 21 communicated with the water tank 1 are provided in the middle frame 2. A penetrating opening 22 for a water supply bracket 7 to pass through is provided in a middle area of the middle frame 2. A plurality of first through holes 23 are provided in an outer side of the penetrating opening 22, and the plurality of first through holes 23 are annularly arranged in the outer side of the penetrating opening 22.

In the present disclosure, the water supply bracket 7 is hollow inside, and a stepped lug boss is constructed at a bottom end of the water supply bracket 7, such that the water supply bracket 7 can be snapped into the penetrating opening 22 of the middle frame 2. The middle frame 2 plays a role of longitudinally supporting the water supply bracket 7. The middle frame 2 may also be arranged above the water tank 1 in other fixing ways. In this embodiment, the water supply bracket 7 can rotate axially around the penetrating opening 22. When the water supply bracket 7 is arranged on the middle frame 2, a lower end of the water supply bracket 7 passes through the penetrating opening 22 and is fixedly connected to a transmission gear 41 arranged below the middle frame.

An annular first gear tray 5 is fixedly connected below the middle frame 2. In this embodiment, the first gear tray 5 is preferably bolt-connected below the middle frame 2. In other embodiments, the first gear tray 5 can be fixed below the middle frame 2 in other ways.

Second through holes corresponding to the first through holes 23 are provided in the first gear tray 5. A gear avoiding hole 51 for accommodating the transmission gear 41 is provided at the center of the first gear tray 5, such that the transmission gear 41 can be connected, transmitted, engaged and so on with other components after passing through the gear avoiding hole 51 of the first gear tray 5. Fog water can also pass through the gear avoiding hole 51 and finally enter the water supply bracket 7.

Rotatory driven gears 42 are provided between the first through holes 23 and the first gear tray 5, and the centers of the driven gears 42 are directly facing the first through holes 23. Bottom ends of rotary decorative pieces 8 are connected to the driven gears 42 at the first through holes 23, and the rotary decorative pieces 8 are driven by the driven gears 42 to rotate during rotation of the driven gears 42.

The first gear tray 5 plays a role in supporting and fixing the driven gears 42, such that the driven gears 42 can rotate between the first through holes 23 and the first gear tray 5.

It is noted that in other alternative embodiments, the second through holes may be eliminated or replaced by a groove formed in the first gear tray 5.

A hollow sleeve (not shown) is fixedly provided in the middle of each of the driven gears 42, the bottom end of each of the rotary decorative pieces 8 is inserted into and fixed in the hollow sleeve after passing through the first through hole 23 in the middle frame 2, and the rotary decorative pieces 8 are driven by the driven gear 42 to rotate during rotation of the driven gears 42. In other alternative embodiments of the present disclosure, the rotary decorative pieces 8 may also be connected to the driven gears 42 in other ways, such as screw connection and fastening connection, which is not limited herein.

The rotary decorative pieces 8 are not limited to cylindrical strips as shown in the drawings. In other alternative embodiments, the rotary decorative pieces 8 may also be constructed as animal-style (such as dragon-style) decorations or planetary-style (such as Saturn-style and Moon-style) decorations, which is not limited herein. The rotary decorative pieces 8 are annularly arranged on the middle frame 2, and the water supply bracket 7 is arranged in the middle of the rotary decorative pieces 8, to achieve a better visual effect.

Figure 3:
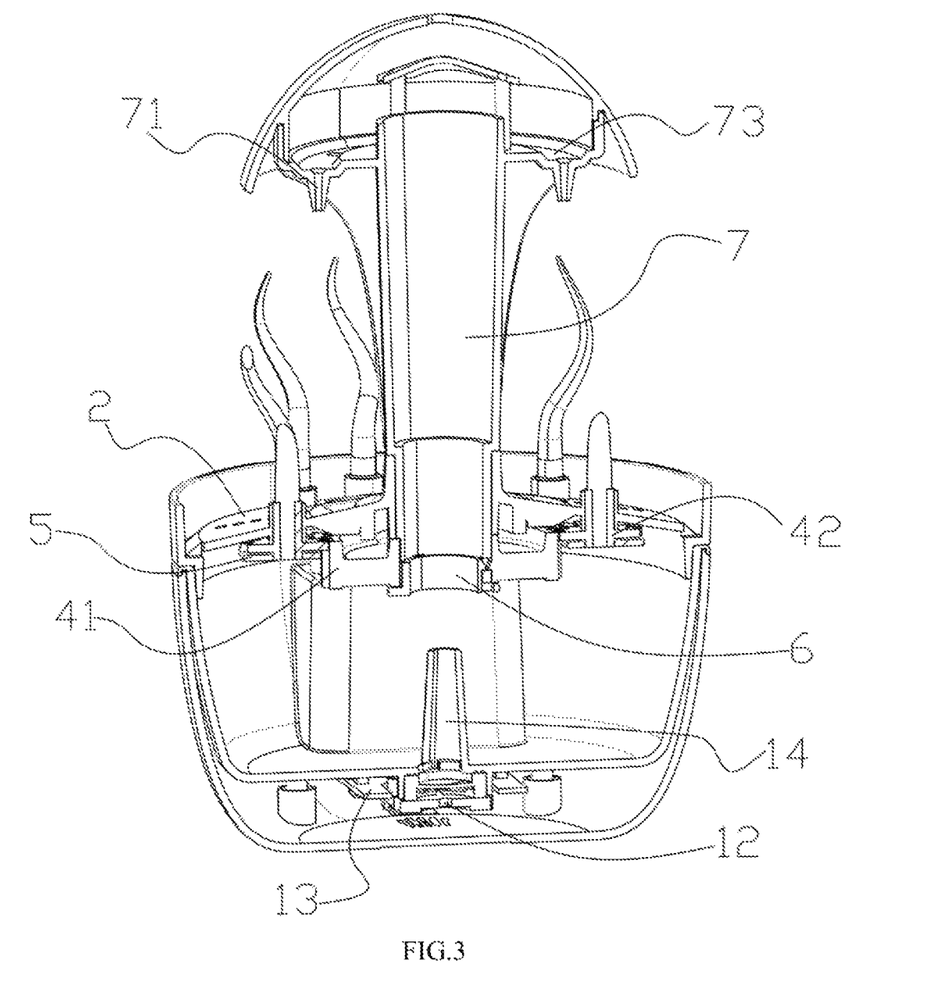
FIG. 3 is a schematic sectional view of Embodiment 1 of the present disclosure.

As shown in FIG. 3, the transmission gear 41 is configured to be hollow in the middle, and passes through the gear avoiding hole 51 to be fixedly connected to the water supply bracket. A second gear tray 6 is provided below the transmission gear 41, and the second gear tray 6 is fastened at the bottom end of the water supply bracket 7 and plays a role in supporting and fixing the transmission gear 41 to prevent the transmission gear 41 from falling off the bottom end of the water supply bracket 7. A water supply hole 61 is provided in the second gear tray 6, such that fog water generated by the atomizing module 12 can pass through the water supply hole 61 and enter the water supply bracket 7.

After the transmission gear 41 is snap-fastened to the bottom end of the water supply bracket 7, the transmission gear 41 is in fixed connection with the water supply bracket 7, and the transmission gear 41 can drive the water supply bracket 7 to rotate integrally during rotation of the transmission gear 41.

Figure 4:
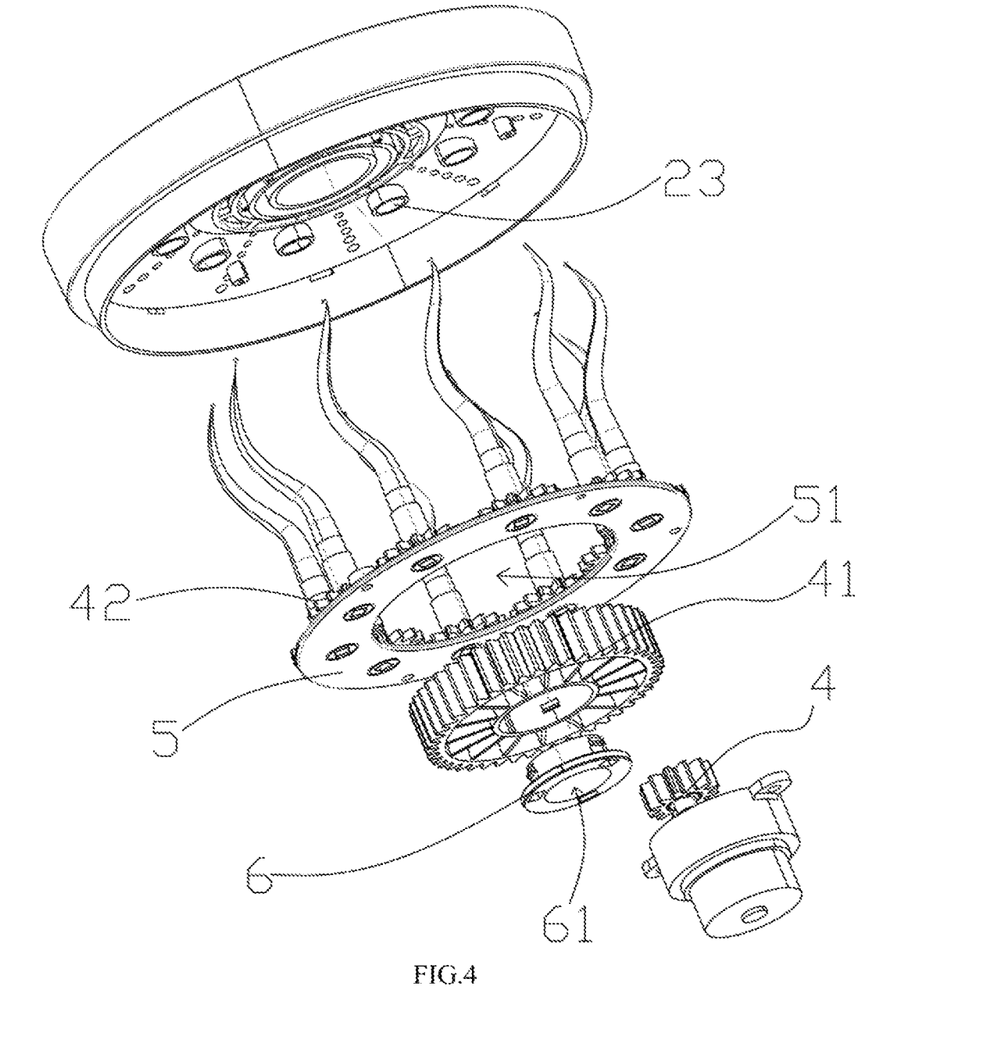
FIG. 4 is a schematic structural exploded diagram of Embodiment 1 of the present disclosure.

As shown in FIG. 4, the driven gears 42 are engaged with the transmission gear 41 at the outer side of the transmission gear 41. Therefore, during rotation of the transmission gear 41, not only the water supply bracket 7, but also the driven gears 42 at the outer side are driven by the transmission gear 41 to rotate. During rotation of the driven gears 42, the rotary decorative pieces 8 are driven by the driven gears 42 to rotate.

The power output component 11 is provided between the water tank 1 and the bottom housing 16. The power output component 11 is arranged within the bin for accommodating the power output component 11. A driving shaft of the power output component 11 stretches into the water tank 1, and a driving gear 4 is fixed on the driving shaft. The driving gear 4 is driven by the driving shaft to rotate during rotation of the driving shaft, and the driving gear 4 is engaged with the transmission gear 41 and drives the transmission gear 41 to rotate, thereby achieving the rotation of the water supply bracket 7 and the rotary decorative pieces 8.

In this embodiment, in order to improve the rotational smoothness of the water supply bracket 7, a bearing (not shown) is provided at the penetrating opening 22 of the middle frame 2. An outer ring of the bearing is fixed into the penetrating opening 22, and an inner ring of the bearing is rotatably arranged on the outer side of the water supply bracket 7. During rotation of the water supply bracket 7, the inner ring of the bearing is driven by the water supply bracket 7 to rotate together, such that the rotational smoothness of the water supply bracket 7 can be improved.

A conducting water-guiding pipe 14 is provided at an upper end of the atomizing module 12 in the water tank 1, and the water-guiding pipe 14 is directly facing the bottom of the water supply bracket 7. When the atomizing module 12 atomizes the water in the water tank 1, the fog water and mist splash upwards (such phenomenon is a common knowledge in the art, so details are not described herein again) and enter the water supply bracket 7 through the water supply hole 61, and finally the water flows into the water storage tray 73 at a top end of the water supply bracket 7. In other alternative embodiments, when a volute atomizing sheet is adopted, the water-guiding pipe 14 can be eliminated because the fog water sprayed by the volute atomizing sheet is converged and sprayed out in one direction, and the water-guiding pipe 14 is not needed to converge the fog water.

Figure 7:
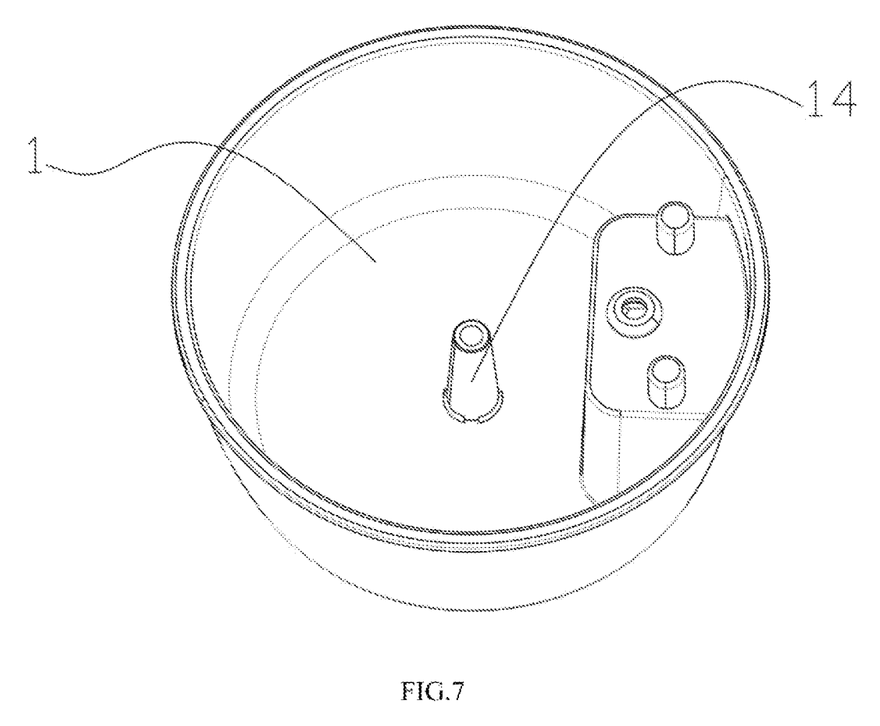
FIG. 7 is a schematic structural diagram of the water tank of Embodiment 1 of the present disclosure.
Figure 8:
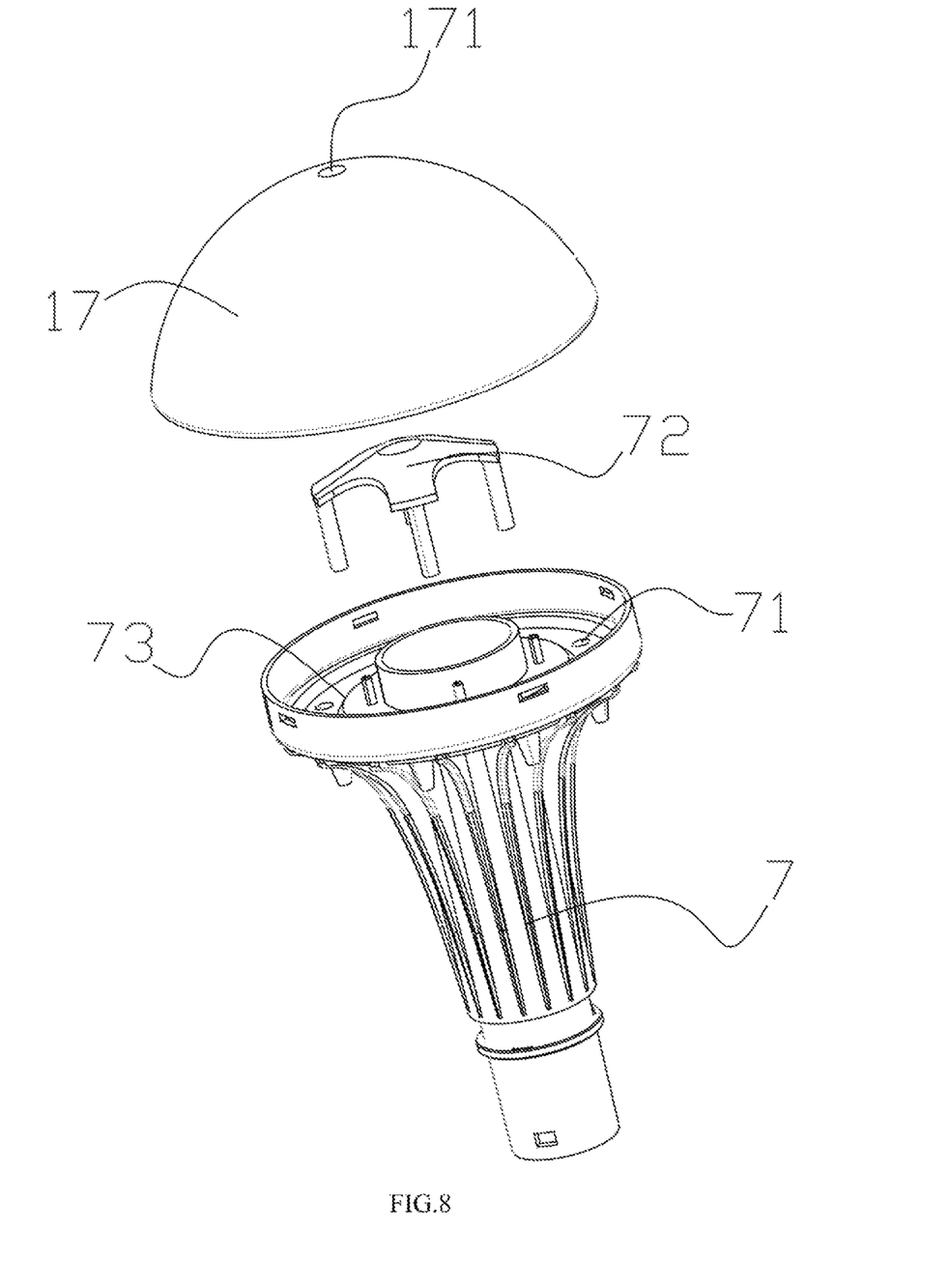
FIG. 8 is a schematic structural exploded diagram of Embodiment 1 of the present disclosure.

As shown in FIG. 7, the water supply bracket 7 is hollow inside, and two ends of the water supply bracket 7 are provided with openings. The water storage tray 73 is provided at the top end of the water supply bracket 7, drip holes 71 are provided in the water storage tray 73, and the fog water sprayed upwards by the atomizing module 12 finally flows into the water storage tray 73 through the inner side of the water supply bracket 7, drips onto the middle frame 2 through the drip holes 71 in the water storage tray 73 and finally flows back into the water tank 1 along the water leakage holes 21 in the middle frame 2.

In a preferred embodiment, the top end of the water supply bracket 7 is higher than the water storage tray 73, such that the water in the water storage tray 73 is prevented from flowing backwards into the water supply bracket 7. A water baffle 72 is provided at the top end of the water supply bracket 7, the water contact surface of the water baffle 72 is arc-shaped, and after the water splashed by the atomizing module 12 strikes the water contact surface of the water baffle 72, the water finally flows into the water storage tray 73 of the water supply bracket 7. Moreover, the water baffle 72 can also prevent the water from being sprayed out from a spray outlet hole 171 in the top cover 17. In this embodiment, the water baffle 72 is detachably fixed on the water storage tray 73 and is directly opposite to the upper side of the water supply bracket 7.

The spray outlet hole 171 is provided at the top end of the top cover 17, the top cover 17 is fastened above the water storage tray 73 of the water supply bracket 7, a spray containing cavity capable of containing the mist is formed by enclosing between the top cover 17 and the water storage tray 73, the spray outlet hole 171 is provided at the top end of the top cover 17, and the mist generated by the atomizing module 12 enters the spray containing cavity through the water supply bracket 7 and is finally sprayed out through the spray outlet hole 171.

The actual operation process of the present disclosure is as follows: a motor drives the driving gear 4 to rotate, the driving gear 4 drives the transmission gear 41 to rotate, and because the transmission gear 41 is rotatably and fixedly connected to the water supply bracket 7, the rotation of the transmission gear 41 drives the water supply bracket 7 to rotate, such that a unique rotating visual effect is achieved. Further, the plurality of driven gears 42 on the outer side are driven by the transmission gear 41 to rotate during rotation of the transmission gear 41, and the driven gears 42 drive the rotary decorative pieces to rotate, such that finally the double rotation of the water supply bracket 7 and the rotary decorative pieces 8 is formed to achieve a unique visual effect.

In addition, in the operation process, the atomizing module 12 supplies the fog water and mist to the water supply bracket 7, and the water finally flows into the water storage tray 73 and drips onto the middle frame 2 through the drip holes 71, such that a unique dripping effect is achieved. The mist in the water supply bracket 7 is sprayed out through the spray outlet hole 171 at the top cover 17, such that a unique spraying effect is achieved.

Figure 9:
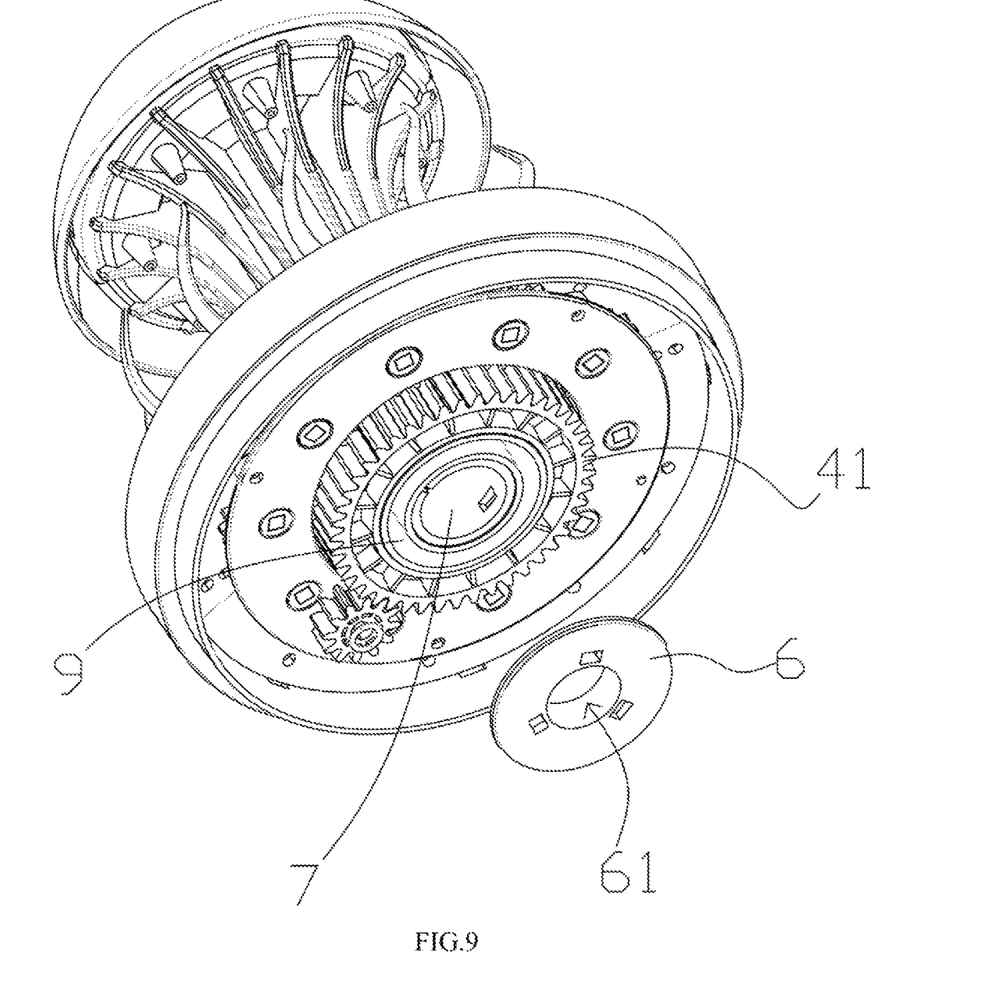
FIG. 9 is a schematic structural exploded diagram of Embodiment 2 of the present disclosure.

As shown in FIG. 9, in a second embodiment of the present disclosure, the water supply bracket 7 is fixedly connected into the penetrating opening 22 of the middle frame 2, the penetrating opening 22 longitudinally fixes the water supply bracket 7, whereas the difference is that the water supply bracket 7 does not rotate axially on the penetrating opening 22.

In particular, a limiting component 9 is provided below the penetrating opening 22 of the middle frame 2, the limiting component 9 is in the shape of an annular opening, the upper part of the limiting component 9 is integrally connected to the lower part of the middle frame 2, and the transmission gear 41 is rotatably arranged on an outer side of the limiting component 9. In another alternative solution, the transmission gear 41 is rotatably provided at the bottom end of the water supply bracket 7, and the transmission gear 41 is not in fixed relationship with the water supply bracket 7. Therefore, during rotation of the transmission gear 41, the water supply bracket 7 is not driven by the transmission gear 41 to rotate and only the driven gears 42 on the outer side are driven by the transmission gear 41 to rotate.

A second gear tray 6 is similarly provided below the transmission gear 41, the second gear tray 6 is fixed in a fastening way onto the limiting component 9 below the penetrating opening 22 or at the bottom of the water supply bracket 7, and the second gear tray 6 configured for fixing and supporting the transmission gear 41, so that the transmission gear 41 is prevented from falling into the water tank 1.

In this embodiment, in order to improve the rotational smoothness of the transmission gear, a bearing (not shown in the figure) is fixed on the inner side of the transmission gear, the outer ring of the bearing is rotatably fixed on the inner side of the transmission gear, the inner ring of the bearing is fixed below the water supply bracket 7 or on an outer side of the limiting component 9, during rotation of the transmission gear, the outer ring of the bearing is driven by the transmission gear to rotate together, so that the rotational smoothness of the transmission gear can be improved.

During the operation of such embodiment, the motor drives the driving gear 4 to rotate, the driving gear 4 drives the transmission gear 41 to rotate, the plurality of driven gears 42 on the outer side are driven by the transmission gear 41 to rotate during rotation of the transmission gear 41, and the driven gears 42 drive the rotary decorative pieces 8 to rotate, so that finally the rotation of the rotary decorative pieces 8 is formed to achieve a unique visual effect.

In the operation process, the atomizing module 12 supplies the fog water and mist to the water supply bracket 7, and the water finally flows into the water storage tray 73 and drips onto the middle frame 2 through the drip holes 71, such that a unique dripping effect is achieved. The mist in the water supply bracket 7 is sprayed out through the spray outlet hole 171 at the top cover 17, so that a unique spraying effect is achieved. The main difference between such embodiment and the previous embodiment is that the transmission gear 41 does not drive the water supply bracket 7 to rotate during rotation of the transmission gear 41.

Various embodiments of the present disclosure are described for illustrative purposes, but the description is not confined to the disclosed embodiments. Without departing from the scopes and the spirits of the described embodiments, many modifications and changes are obvious for persons of ordinary skill in the art. The terms in the embodiments are used for best explain the principles and the practical applications of the embodiments or enabling other persons of ordinary skill in the art to understand the embodiments disclosed herein, and therefore cannot be understood as the limitation to the present disclosure.

What is claimed is:

1. A rotary dripping aromatherapy humidifier, comprising a water tank, wherein an atomizing module and a power output component are fixedly provided below the water tank, a driving gear is provided on the power output component, the driving gear is positioned inside the water tank, and a middle frame is covered on the water tank, wherein:

a penetrating opening is provided on the middle frame, a hollow water supply bracket is provided within the penetrating opening, and a transmission gear is provided below the water supply bracket; and water leakage holes and at least one first through hole are provided in the middle frame, a first gear tray is provided below the middle frame, a gear avoiding hole for the transmission gear to pass through is provided in the first gear tray, rotatable driven gears corresponding to the at least one first through hole are provided between the first gear tray and the middle frame, and rotary decorative pieces are fixedly provided on the driven gears.

2. The rotary dripping aromatherapy humidifier of claim 1, wherein the water supply bracket is rotatably arranged at the penetrating opening, a lower part of the water supply bracket is fixedly connected to the transmission gear, and the water supply bracket rotates together with the transmission gear during rotation of the transmission gear.

3. The rotary dripping aromatherapy humidifier of claim 1, wherein the water supply bracket is fixedly arranged in the penetrating opening.

4. The rotary dripping aromatherapy humidifier of claim 3, wherein a limiting component is fixedly provided below the penetrating opening, and the transmission gear is rotatably arranged on an outer side of the limiting component or below the water supply bracket.

5. The rotary dripping aromatherapy humidifier of claim 2, wherein the driving gear, the transmission gear and the driven gears are in engaged transmission, and the rotary decorative pieces are driven by the driven gears to rotate during rotation of the driven gears.

6. The rotary dripping aromatherapy humidifier of claim 1, wherein a second gear tray configured for supporting the transmission gear is provided below the transmission gear, a water supply hole is provided in the second gear tray, and the second gear tray is fixed below the water supply bracket or below the penetrating opening.

7. The rotary dripping aromatherapy humidifier of claim 1, wherein a bearing is provided on an outer side of the water supply bracket or on an inner side of the transmission gear.

8. The rotary dripping aromatherapy humidifier of claim 1, wherein a water storage tray is provided at an upper end of the water supply bracket, and drip holes for dripping water are provided in the water storage tray.

9. The rotary dripping aromatherapy humidifier of claim 8, wherein a top cover is covered on the water storage tray, a spray outlet hole is provided in the top cover, and a water baffle is provided below the spray outlet hole.

10. The rotary dripping aromatherapy humidifier of claim 1, wherein the rotary decorative pieces are annularly arranged on the middle frame, and the water supply bracket is arranged at a center of the rotary decorative pieces.

* * * * *